(12) United States Patent
Higuchi et al.

(10) Patent No.: US 8,860,097 B2
(45) Date of Patent: Oct. 14, 2014

(54) FIELD EFFECT TRANSISTOR TYPE BIOSENSOR

(75) Inventors: Takuya Higuchi, Tokyo-to (JP); Tomonori Akai, Tokyo-to (JP); Katsuyuki Motai, Tokyo-to (JP)

(73) Assignee: Dai Nippon Printing Co., Ltd., Tokyo-to (JP)

(*) Notice: Subject to any disclaimer, the term of this patent is extended or adjusted under 35 U.S.C. 154(b) by 0 days.

(21) Appl. No.: 13/701,610

(22) PCT Filed: Jun. 14, 2011

(86) PCT No.: PCT/JP2011/063607
§ 371 (c)(1),
(2), (4) Date: Dec. 3, 2012

(87) PCT Pub. No.: WO2011/158836
PCT Pub. Date: Dec. 22, 2011

(65) Prior Publication Data
US 2013/0075793 A1  Mar. 28, 2013

(30) Foreign Application Priority Data

Jun. 14, 2010 (JP) .................... 2010-134734

(51) Int. Cl.
*H01L 29/66* (2006.01)
*H01L 29/78* (2006.01)
*G01N 27/414* (2006.01)

(52) U.S. Cl.
CPC ............ *H01L 29/78* (2013.01); *G01N 27/4145* (2013.01)
USPC ........................................... 257/252; 257/253

(58) Field of Classification Search
CPC .............................. H01L 29/82; G01N 27/414
USPC .................... 257/252, 253; 438/49, 151
See application file for complete search history.

(56) References Cited

U.S. PATENT DOCUMENTS

| 7,989,851 B2 * | 8/2011 | Lu et al. ............. 257/252 |
| 2007/0095664 A1 * | 5/2007 | Chou et al. .......... 204/433 |

FOREIGN PATENT DOCUMENTS

| JP | 2005-195492 A | 7/2005 |
| JP | 2007-108160 A | 4/2007 |
| JP | 2008-216038 A | 9/2008 |
| JP | 2008-286714 A | 11/2008 |
| JP | 2009-002839 A | 1/2009 |

OTHER PUBLICATIONS

International Search Report: PCT/JP2011/063607.

* cited by examiner

*Primary Examiner* — Timor Karimy
(74) *Attorney, Agent, or Firm* — Ladas & Parry LLP

(57) ABSTRACT

Provided is a biosensor that makes it possible to detect the electrical properties of a bio-related material contained in an analyte fluid such as an aqueous solution placed on a sensitive membrane and to observe the bio-related material at a high magnification with an observation device such as a microscope. The biosensor comprises: a substrate 10, a transparent semiconductor film 20 laminated on the substrate 10, a source electrode 30a and a drain electrode 30b formed at both ends of the transparent semiconductor film 20, an insulating film 40 laminated so as to cover the transparent semiconductor film 20 and the source electrode 30a and the drain electrodes 30b, a sensitive membrane 50 laminated on the insulating film 40, and a partition 60 that is formed at both ends of the sensitive membrane 50 to retain an analyte fluid 100, such as an aqueous solution or liquid culture containing a sample, on the sensitive membrane 50 and to retain the analyte fluid 100 in a specific region so that the bio-related material 200 can be placed on the sensitive membrane 50.

9 Claims, 7 Drawing Sheets

FIELD EFFECT TRANSISTOR TYPE BIOSENSOR

TECHNICAL FIELD

The invention relates to a biosensor using a semiconductor field-effect transistor.

BACKGROUND ART

In recent years, a variety methods for examination of bio-related materials such as DNA, sugar chains, and proteins have been developed for certain purposes such as diagnosis of diseases, detection of individual differences in drug metabolism, or food or environmental monitoring, and in particular, biosensors for detecting biomolecules based on electric signals have been studied. Recently, many studies have been made on biosensors for detecting biological reactions by means of a field effect transistor (hereinafter also referred to as "FET"), in view of fast conversion of electric signals and easiness in connection between an integrated circuit and a micro electro mechanical system (MEMS).

A conventional FET biosensor has a structure comprising: a MOSFET from which the gate electrode is removed; and an ion sensitive membrane deposited on the insulating film, and such a structure is called "ISFET (Ion Sensitive FET)." Such a structure can function as various biosensors when oxidoreductases, various proteins, DNAs, antigens, antibodies, etc. are placed on the ion sensitive membrane (for example, Patent Literature 1).

Specifically, a FET used in a biosensor comprises a silicon substrate; a source electrode, a drain electrode, and a gate insulating film, which are formed on the surface of the silicon substrate; and a metal electrode formed on the surface of the gate insulator between the source and drain electrodes. A DNA probe and alkanethiol are placed on the surface of the metal electrode. In practical measurement, the metal electrode, the DNA probe and alkanethiol placed on the surface of the metal electrode, and a reference electrode are placed in a reaction solution in a measurement cell. When a high frequency voltage is applied through the reference electrode, the electrical characteristics of the insulated gate field-effect transistor will change before and after the target DNA contained in the reaction solution binds to the DNA probe. Therefore, whether or not the target DNA in the reaction solution is extended can be determined by detecting a change in the electrical characteristics of the transistor, specifically a change in the value of the current through the source and the drain.

CITATION LIST

Patent Literature

Patent Literature 1: Japanese Patent Application Publication Laid-Open No. 2007-108160

SUMMARY OF INVENTION

Technical Problem

In general, when the state of a bio-related material such as cells or DNA is detected based on electric signals, observation of the state of cells or DNA with a microscope and electrical signal characteristics in that state are important factors. On the other hand, it is usually desired to observe cells or other materials at a high magnification with transmitted light.

Unfortunately, when the biosensor described in Patent Literature 1 is used, a bio-related material contained in an analyte fluid placed on the ion sensitive membrane cannot be observed at a high magnification because of the non-transparent base material and the non-transparent source or drain electrode.

To observe a bio-related material at a high magnification, it is necessary to bring the observation surface of the object lens of a microscope or the like closer to the placed bio-related material. However, when a bio-related material placed on the ion sensitive membrane is observed from above (from the side opposite to the substrate side), the analyte fluid itself containing the bio-related material, such as an aqueous solution, a liquid culture, or other chemical agents, becomes a factor of inhibiting the observation, and it is difficult to observe the placed bio-related material at a high magnification by bringing the observation surface of the object lens of a microscope or the like closer to the ion sensitive membrane. In addition, since the base material and the electrodes are made of non-transparent materials, the sample placed on the ion sensitive membrane cannot be observed from the base material side.

The present invention has been made to solve the above problems, and an object of the invention is to provide a biosensor that makes it possible not only to detect the electrical properties of a bio-related material contained in an analyte fluid placed on a sensitive membrane but also to observe the placed bio-related material at a high magnification with an observation device such as a microscope.

Solution to Problem (1) To solve the above problems, the field effect transistor type biosensor of the invention comprises: a transparent substrate; a transparent semiconductor film laminated on the transparent substrate; a source electrode and a drain electrode formed at both ends of the semiconductor film; and a sensitive membrane that is laminated on the semiconductor film with an insulating film interposed therebetween and has an upper surface on which a bio-related material contained in an analyte fluid is to be placed.

According to the invention, the bio-related material placed on the sensitive membrane can be observed from the substrate side using a microscope or any other optical observation device, while light is applied from above the analyte fluid (from the side opposite to the substrate side), so that the bio-related material can be accurately observed at a high magnification as compared with the case where the bio-related material placed on the sensitive membrane is observed from above the analyte fluid and that detection of the electrical properties of the bio-related material and high-magnification observation of the bio-related material can be achieved at the same time.

(2) The field effect transistor type biosensor of the invention may further comprise: a first region that has hydrophilicity; and that is formed on the upper surface of the sensitive membrane, on which the bio-related material is to be placed, and on at least above the channel of the semiconductor film; and a second region that has hydrophobicity; and that is formed adjacent to the first region and in the horizontal direction perpendicular to a laminating direction of the first region.

According to the invention, the need for a partition and other members for retaining the analyte fluid on the sensitive membrane can be eliminated, so that the analyte fluid can be retained on the sensitive membrane without any partition and that the process of manufacturing the biosensor can be simplified.

(3) The field effect transistor type biosensor of the invention may further comprise: a first region that has cell adhesive properties; and that is formed on the upper surface of the sensitive membrane, on which the bio-related material is to be placed, and on at least above the channel of the semiconductor film; and a second region that has cell adhesion-inhibiting properties, comprises a hydrophilic film containing an organic compound with a carbon-oxygen bond, and is formed adjacent to the first region and in the horizontal direction perpendicular to the laminating direction of the first region.

Usually, cells collect at the bottom of the analyte fluid on the sensitive membrane due to gravity. According to the invention, the bio-related material can be concentrated on the cell adhesive region and prevented from being deposited on the cell adhesion-inhibiting region, so that the effect of the bio-related material present on regions other than the cell adhesive region can be eliminated in the process of detecting the electrical properties, which makes it possible to accurately detect the electrical properties of the bio-related material adhering to the cell adhesive region.

(4) The field effect transistor type biosensor of the invention may further comprise a reference electrode that is for applying a variable voltage to the analyte fluid and is provided adjacent to the sensitive membrane in such a manner as to be insulated from the source electrode and the drain electrode.

According to the invention, a reference voltage can be applied to the analyte fluid through the reference electrode simply by retaining the analyte fluid on the sensitive membrane without inserting a reference electrode into the analyte fluid after the analyte fluid is retained on the sensitive membrane, so that the examination process can be made simple.

(5) In the field effect transistor type biosensor of the invention, the reference electrode may be a transparent electrode.

According to the invention, the reference electrode can be a transparent electrode, so that the bio-related material contained in the analyte fluid can be observed at a high magnification with an observation device such as a microscope.

(6) In the field effect transistor type biosensor of the invention, the transparent semiconductor film may comprise a transparent oxide semiconductor.

According to the invention, the transparent semiconductor film can be made of a transparent oxide semiconductor, so that the bio-related material contained in the analyte fluid can be observed at a high magnification with an observation device such as a microscope.

(7) In the field effect transistor type biosensor of the invention, the source electrode and the drain electrode may each comprise a transparent electrode.

According to the invention, the source electrode and the drain electrode can each be made of a transparent electrode such as an ITO or IZO electrode, so that the bio-related material contained in the analyte fluid can be observed at a high magnification with an observation device such as a microscope.

(8) In the field effect transistor type biosensor of the invention, the substrate may comprise any of glass, PEN, or PET.

According to the invention, the substrate can be made of any of glass, PEN, or PET, so that the bio-related material contained in the analyte fluid can be observed at a high magnification with an observation device such as a microscope.

(9) In the field effect transistor type biosensor of the invention, the sensitive membrane may have a placement region at least on which the bio-related material is to be placed, and the biosensor of the invention may further comprise a partition that is formed around the placement region to retain the analyte fluid on the placement region.

According to the invention, by means of the partition, the analyte fluid can be retained on the placement region of the sensitive membrane, where the bio-related material is deposited, which makes it possible to accurately detect the electrical properties of the bio-related material.

Advantageous Effects of Invention

When the biosensor of the invention is used, the bio-related material placed on the sensitive membrane can be observed from the substrate side using a microscope or any other optical observation device, while light is applied from above the analyte fluid (from the side opposite to the substrate side), so that the bio-related material can be observed at a high magnification as compared with that achieved when the bio-related material placed on the sensitive membrane is observed from above the analyte fluid and that detection of the electrical properties of the bio-related material and high-magnification observation of the bio-related material can be achieved at the same time.

DESCRIPTION OF EMBODIMENTS

Hereinafter, embodiments of the invention are described with reference to the drawings, respectively. The embodiments described below are in cases where the field effect transistor type biosensor of the invention is used to form an ISFET biosensor having such a structure that a sample, specifically a bio-related material such as cells, DNA, sugar chains, and proteins (hereinafter also referred to as "sample"), contained in an analyte fluid placed on a sensitive membrane can be visualized from the substrate side by a microscope. The ISFET used in the ISFET biosensor of each of FIGS. 1 to 6 has a pseudo top gate bottom contact structure, and the ISFET used in the ISFET biosensor of FIG. 7 has a pseudo top gate top contact structure.

First Embodiment

Figure 1:
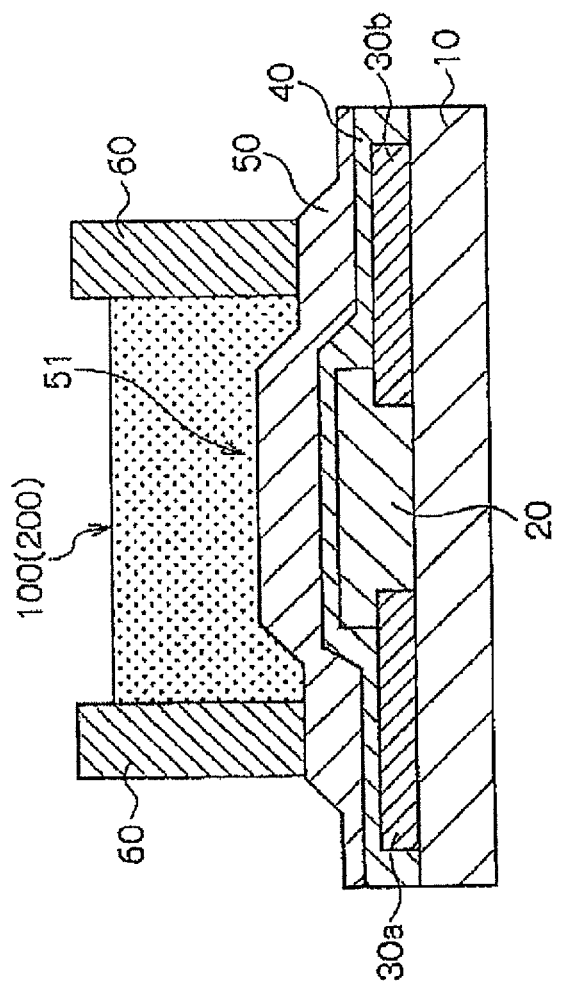
FIG. 1 is a cross-sectional view of an ISFET biosensor according to a first embodiment of the invention.
Figure 2:
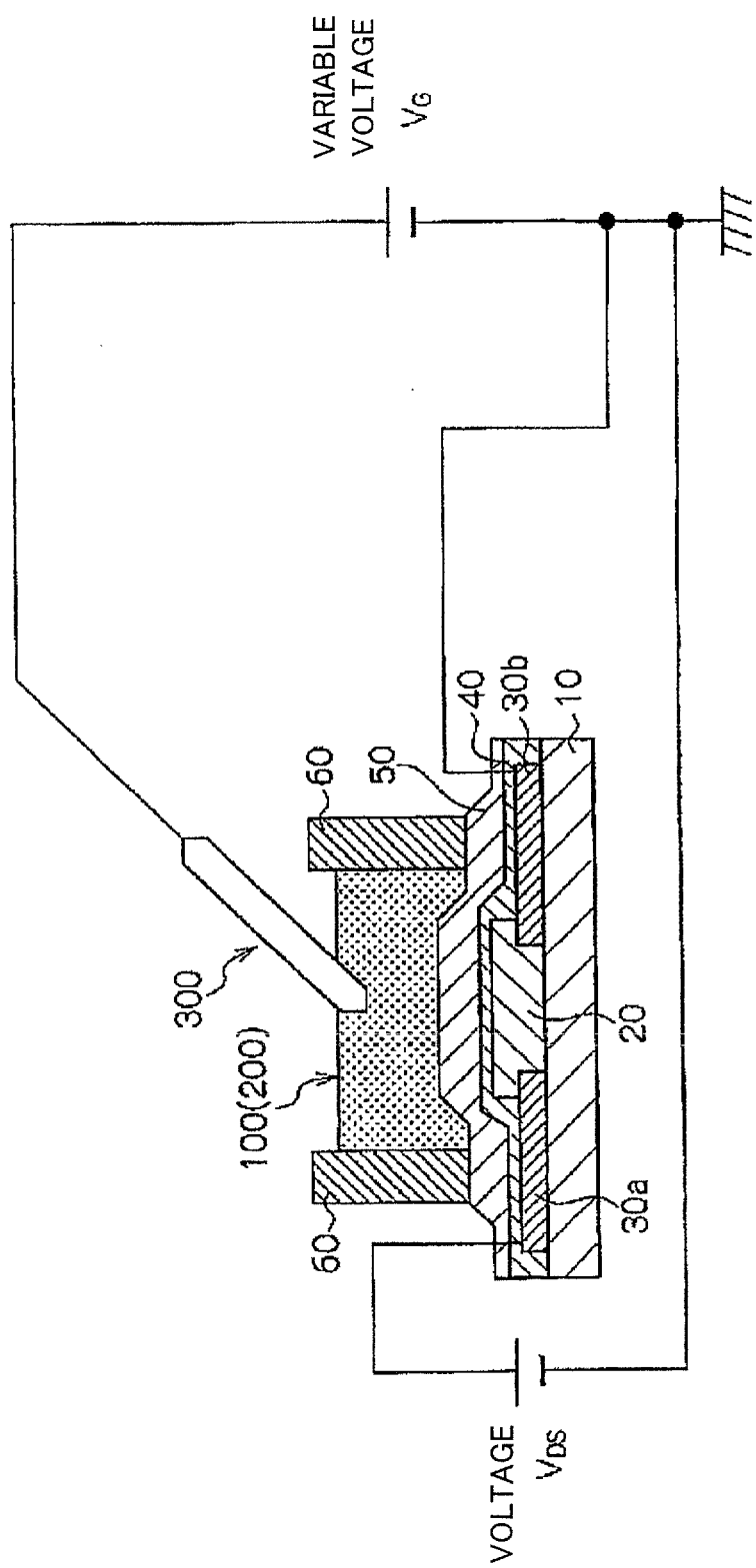
FIG. 2 is a diagram for illustrating the principle of operation of the ISFET biosensor according to the first embodiment.

First, an ISFET biosensor according to a first embodiment of the invention is described using FIGS. 1 and 2.
(Structure of ISFET Biosensor)
First, the structure of the ISFET biosensor of this embodiment is described using FIG. 1. FIG. 1 is a cross-sectional view of the ISFET biosensor of this embodiment.

As shown in FIG. 1, the ISFET biosensor of this embodiment comprises: a substrate 10, a transparent semiconductor film 20 laminated on the substrate 10, a source electrode 30a and a drain electrode 30b formed at both ends of the transparent semiconductor film 20, an insulating film (also referred to as "gate insulating film") 40 laminated so as to cover the transparent semiconductor film 20 and the source and drain electrodes 30a and 30b, a sensitive membrane 50 laminated on the insulating film 40, and a partition 60 that is formed at both ends of the sensitive membrane 50 to retain an analyte fluid 100, such as an aqueous solution or liquid culture containing a sample, on the sensitive membrane 50.

The substrate 10 may be made of any material that is transparent so that the sensitive membrane 50 can be observed from below the substrate 10, and allows the lamination of the transparent semiconductor film 20 and the source and drain electrodes 30a and 30b thereon. The transparency of the substrate may be at such a level that the bio-related material 200 placed on the sensitive membrane 50 can be observed through the substrate 10 using an observation device such as a microscope, and such transparency is not intended to include semi-transparency. Examples of such a material include an inorganic material such as glass and an organic material typified by a plastic such as PEN or PET (a polyester resin, a polyethylene resin, a polypropylene resin, an ABS resin, nylon, an acrylic resin, a fluororesin, a polycarbonate resin, a polyurethane resin, a methyl pentene resin, a phenol resin, a melamine resin, an epoxy resin, or a vinyl chloride resin). The substrate 10 may also be in any form, such as a flat form such as a flat plate, a flat membrane, a film, or a porous membrane, or a three-dimensional form such as a cylinder, a stamp, a multi-well plate, or a micro flow channel. When a film is used, the thickness of the film is generally, but not limited to, about 1 µm to about 1 mm.

The transparent semiconductor film 20 is a layer laminated on the substrate 10. The transparent semiconductor film 20 may be made of any material that is transparent so that the sensitive membrane 50 can be observed from below the substrate 10, and allows the placement of the insulating film 40 thereon. Similarly to the substrate 10, the transparency of the film may be at such a level that the bio-related material 200 placed on the sensitive membrane 50 can be observed through the substrate 10 using an observation device such as a microscope, and such transparency is not intended to include semi-transparency.

Specifically, the transparent semiconductor film 20 may be made of an amorphous oxide based on InMZnO (wherein M is at least one of gallium (Ga), aluminum (Al), and iron (Fe)). In particular, an InGaZnO-based amorphous oxide, which contains Ga as the M element, is preferred. If necessary, the transparent semiconductor film 20 based on the IGZO may also be doped with Al, Fe, Sn, or any other constituent element. The transparent semiconductor film 20 including the IGZO semiconductor film or the like can be formed at a low temperature from room temperature to about 150° C. and therefore is preferably formed on a less heat-resistant plastic or glass substrate.

Alternatively, the transparent semiconductor film 20 may be made of an oxide semiconductor based on zinc oxide (ZnO). The transparent semiconductor film 20 based on ZnO may be not only an intrinsic zinc oxide film but also a film containing, as needed, any of zinc oxide doped with a p-type dopant such as lithium (Li), sodium (Na), nitrogen (N), or carbon (C), zinc oxide doped with an n-type dopant such as boron (B), aluminum (Al), gallium (Ga), or indium (In), and zinc oxide doped with magnesium (Mg), beryllium (Be), or any other element. The transparent semiconductor film 20 may also be made of an oxide semiconductor such as tin-doped indium oxide (indium tin oxide (ITO)), indium zinc oxide (IZO), or magnesium oxide (MgO).

The thickness of the transparent semiconductor film 20 may be selected as needed depending on various conditions. In particular, it is preferably from about 20 nm to about 100 nm.

The source electrode 30a and the drain electrode 30b are formed at both ends of the transparent semiconductor film 20, specifically, formed adjacent to each other in the horizontal direction perpendicular to the laminating direction. The source electrode 30a and the drain electrode 30b may each be made of any material that can form an ohmic contact with the transparent semiconductor film 20, can each be a transparent electrode so that the sensitive membrane 50 can be observed from below the substrate 10, and each be formed by an electronically-conductive film which allows the lamination of the insulating film 40 thereon. Similarly to the substrate 10, the transparency of the electrodes may be at such a level that the bio-related material 200 placed on the sensitive membrane 50 can be observed through the substrate 10 using an observation device such as a microscope, and such transparency is not intended to include semi-transparency. Specifically, the electrodes may each be made of an electrically-conductive material such as indium tin oxide (ITO), indium zinc oxide (IZO), zinc oxide (ZnO), or tin oxide ($SnO_2$).

The thickness of each of the source electrode 30a and the drain electrode 30b may be selected as needed depending on various conditions. In particular, it is preferably from about 20 nm to about 200 nm.

The insulating film 40 is laminated on the transparent semiconductor film 20 and the source and drain electrodes 30a and 30b so as to cover the transparent semiconductor film 20 and the source and drain electrodes 30a and 30b. The insulating film 40 may be made of any material that is transparent so that the sensitive membrane 50 can be observed from below the substrate 10, and allows the lamination of the sensitive membrane 50 thereon. Specifically, the insulating film 40 may be made of a silicon oxide material or silicon nitride material such as silicon oxide ($SiO_2$), silicon nitride ($SiN_x$), or silicon nitride oxide ($SiO_xN_y$) in view of insulating properties. In particular, silicon oxide is preferably used to form the insulating film 40 in this embodiment. The thickness of the insulating film 40 is preferably from about 50 nm to about 1 µm while it may be selected as needed depending on various conditions.

The sensitive membrane 50, which is laminated on the insulating film 40, may be made of a material that allows the placement thereon of a sample contained in the analyte fluid 100, specifically the bio-related material 200 such as cells, DNA, sugar chains, or proteins. Specifically, the sensitive membrane 50 has at least a region 51 at which the bio-related material 200 in the retained analyte fluid 100 will be placed on the channel-forming region of the transparent semiconductor film 20 (hereinafter, such a region is referred to as "placement region"). The sensitive membrane 50 may be an ion sensitive membrane made of a silicon oxide ($SiO_2$) film, a silicon nitride ($SiN_4$) film, a tantalum oxide ($Ta_2O_5$) film, or an aluminum oxide ($Al_2O_3$) film. These ion sensitive membranes may be used as needed, depending on the ion species to be measured. If necessary, the sensitive membrane may also be subjected to surface modification for immobilizing DNA, proteins, or sugar chains.

The partition 60 is formed on the sensitive membrane 50 and around the placement region 51. The partition 60 has a specific height so that the analyte fluid 100 such as an aqueous solution or a liquid culture can be retained on the sensitive membrane 50 along the laminating direction. The partition may be made of any material that can prevent the analyte fluid 100 from leaking out of the placement region 51. Specifically, the partition may be made of glass, plastic, or metal.

(Principle of Operation of ISFET Biosensor)

Next, the principle of operation of the ISFET biosensor in this embodiment is described using FIG. 2. FIG. 2 is a diagram for illustrating the principle of operation of the ISFET biosensor in this embodiment.

The ISFET biosensor of this embodiment having the structure described above is configured to allow the placement of the sample in the analyte fluid 100, specifically the bio-related material 200 such as cells, DNA, sugar chains, or proteins, on the sensitive membrane 50. As shown in FIG. 2, therefore, while a voltage $V_{DS}$ of about 0.1 V to about 1 V is applied between the source and the drain, a variable voltage (reference voltage) $V_G$ may be applied to the analyte fluid 100 through a reference electrode 300 inserted in the analyte fluid 100, so that the channel region formed in the transparent semiconductor film 20 can be changed according to a change in the electric potential (hereinafter also referred to as "film potential") generated on the sensitive membrane 50, which makes it possible to detect a change in drain current $I_D$. As a result, the change in drain current $I_D$ based on the reference voltage $V_G$, specifically the current-voltage characteristics of the transistor, can be compared with the current-voltage characteristics for the bio-related material 200, which have been measured previously, so that the type of the sample in the analyte fluid 100 can be identified.

On the other hand, light may be applied from above the analyte fluid 100 (from the side opposite to the substrate 10 side) (not shown), and the bio-related material 200 placed on the sensitive membrane 50 may be observed from the substrate 10 side using a microscope or any other optical observation device. Particularly when an inverted microscope is used with the aid of transmitted light, the objective lens can be brought closer to the bio-related material 200 placed on the sensitive membrane 50. Besides the bright field observation, if necessary, observation may be performed using a phase contrast microscope, a differential interference microscope, or any other microscope. Therefore, the biosensor is designed to make it possible, at the same time, to detect the electrical properties of the bio-related material 200 placed on the sensitive membrane 50 and to observe the bio-related material 200 at a high magnification.

Advantageous Effects

As described above, when the ISFET biosensor of this embodiment is used, the bio-related material 200 placed on the sensitive membrane 50 can be observed from the substrate 10 side using a microscope or any other optical observation device, while light is applied from above the analyte fluid 100 (from the side opposite to the substrate 10 side), so that the bio-related material 200 can be observed at a high magnification as compared with that achieved when the bio-related material 200 placed on the sensitive membrane 50 is observed from above the analyte fluid 100 and that detection of the electrical properties of the bio-related material 200 and high-magnification observation of the bio-related material 200 can be achieved at the same time.

The ISFET biosensor of this embodiment has the transparent semiconductor film 20, which may be made of a transparent oxide semiconductor. Therefore, provided is a biosensor with which the bio-related material 200 contained in the analyte fluid 100 can be observed at a high magnification using an observation device such as a microscope.

The ISFET biosensor of this embodiment has the source and drain electrodes 30a and 30b, which may be made of transparent electrodes, in which the transparent electrodes may be made of either ITO or IZO. Therefore, provided is a biosensor with which the bio-related material 200 contained in the analyte fluid 100 can be observed at a high magnification using an observation device such as a microscope.

The ISFET biosensor of this embodiment has the substrate 10, which may be made of any of glass, PEN, or PET. Therefore, provided is a biosensor with which the bio-related material 200 contained in the analyte fluid 100 can be observed at a high magnification using an observation device such as a microscope.

In the ISFET biosensor of this embodiment, the partition 60 allows the analyte fluid 100 to be retained on the replacement region 51 of the sensitive membrane 50, at which the bio-related material 200 is placed, so that the electrical properties of the bio-related material 200 can be detected accurately.

Second Embodiment

Figure 3:
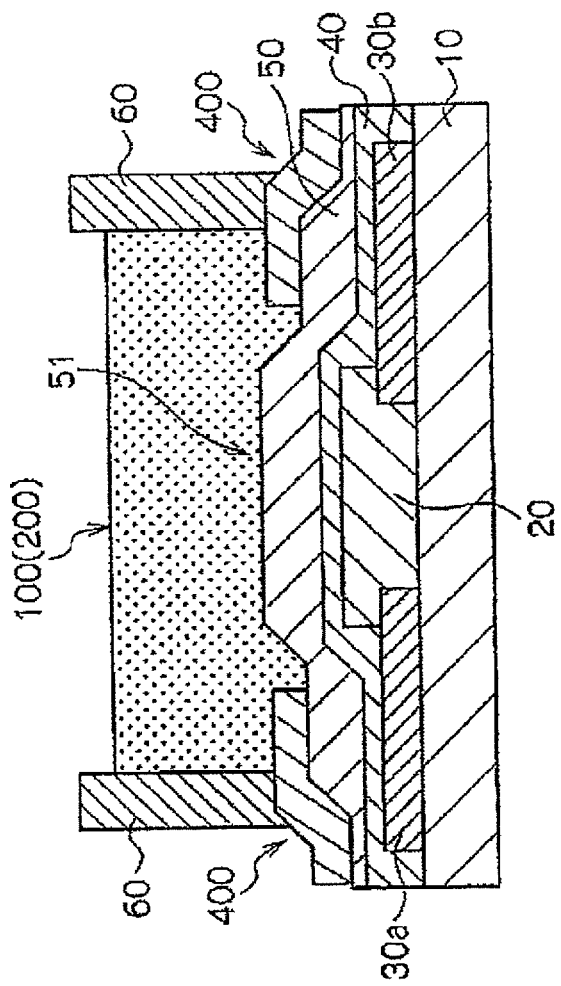
FIG. 3 is a cross-sectional view of an ISFET biosensor according to a second embodiment of the invention.
Figure 4:
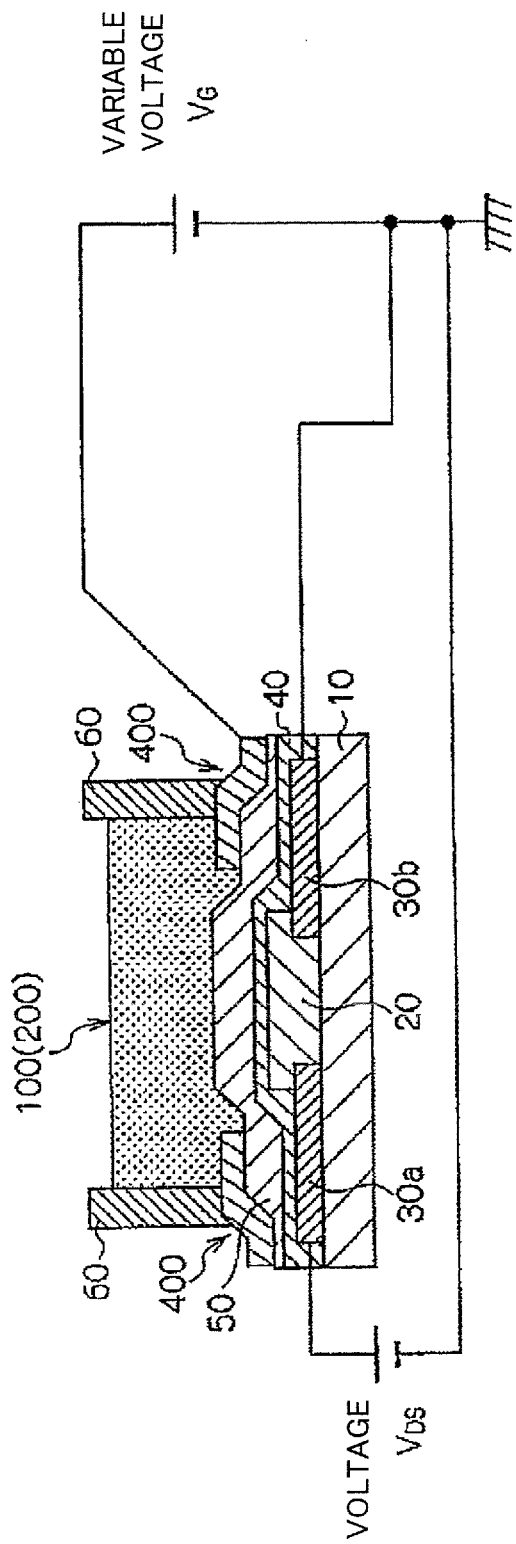
FIG. 4 is a diagram for illustrating the principle of operation of the ISFET biosensor according to the second embodiment.

Next, an ISFET biosensor according to a second embodiment of the invention is described using FIGS. 3 and 4.

The ISFET biosensor of this embodiment is characterized by comprising a reference electrode 400, which is transparent, provided instead of the reference electrode 300 inserted in the analyte fluid 100 in the first embodiment, and formed adjacent to the sensitive membrane 50 and in a region where a reference voltage can be applied to the analyte fluid 100. The other features are the same as the first embodiment. Therefore, the same components are represented by the same reference signs, and the description thereof is omitted.

(Structure of ISFET Biosensor)

First, the structure of the ISFET biosensor of this embodiment is described using FIG. 3. FIG. 3 is a cross-sectional view of the ISFET biosensor of this embodiment.

As shown in FIG. 3, the ISFET biosensor of this embodiment comprises: a substrate 10, a transparent semiconductor film 20 laminated on the substrate 10, source and drain electrodes 30a and 30b formed at both ends of the transparent semiconductor film 20, an insulating film 40 laminated so as to cover the transparent semiconductor film 20 and the source and drain electrodes 30a and 30b, a sensitive membrane 50 laminated on the insulating film 40, a transparent reference electrode 400 which is for applying a reference voltage to an analyte fluid 100 and placed adjacent to the placement region 51 of the sensitive membrane 50, and a partition 60 for retaining an analyte fluid 100, such as an aqueous solution or liquid culture containing a sample, on the sensitive membrane 50.

The transparent reference electrode 400 is formed adjacent to the placement region 51 of the sensitive membrane 50 in the horizontal direction perpendicular to the laminating direction. The transparent reference electrode 400 is formed at an analyte fluid 100-retaining region so that part of it can come into contact with the analyte fluid 100. In addition, the transparent reference electrode 400 is provided so as to be insulated from the source and drain electrodes 30a and 30b, and laminated on a region other than the placement region 51 of the sensitive membrane 50. The transparent reference electrode 400 may be made of any type of transparent electrically-conductive film. Similarly to the substrate 10, the transparency of the reference electrode may be at such a level that the bio-related material 200 placed on the sensitive membrane 50 can be observed through the substrate 10 using an observation device such as a microscope, and such transparency is not intended to include semi-transparency. Specifically, the reference electrode may be made of an electrically-conductive material such as indium tin oxide (ITO), indium zinc oxide (IZO), zinc oxide (ZnO), or tin oxide ($SfO_2$).

(Operation of ISFET Biosensor)

Next, the principle of operation of the ISFET biosensor in this embodiment is described using FIG. 4. FIG. 4 is a diagram for illustrating the principle of operation of the ISFET biosensor in this embodiment.

The ISFET biosensor of this embodiment having the structure described above is configured to allow the placement of the sample in the analyte fluid 100, specifically the bio-related material 200 such as cells, DNA, sugar chains, or proteins, on the sensitive membrane 50. Similarly to the first embodiment, therefore, as shown in FIG. 4, while a voltage $V_{DS}$ of about 0.1 V to about 1 V is applied between the source and the drain, a variable voltage (reference voltage) $V_G$ may be applied to the analyte fluid 100 through the reference electrode 400, so that the channel region formed in the transparent semiconductor film 20 can be changed according to a change in the film potential generated on the sensitive membrane 50, which makes it possible to detect a change in drain current $I_D$. As a result, the change in drain current $I_D$ based on the reference voltage $V_G$, specifically the current-voltage characteristics, can be compared with the current-voltage characteristics for the bio-related material 200, which have been measured previously, so that the type of the sample in the analyte fluid 100 can be identified.

On the other hand, as in the first embodiment, light may be applied from above the analyte fluid 100 (from the side opposite to the substrate 10 side) (not shown), and the bio-related material 200 placed on the sensitive membrane 50 may be observed from the substrate 10 side using a microscope or any other optical observation device. Therefore, the biosensor is designed to make it possible, at the same time, to detect the electrical properties of the bio-related material 200 placed on the sensitive membrane 50 and to observe the bio-related material 200 at a high magnification.

Advantageous Effects

The ISFET biosensor of this embodiment has the advantageous effect of the first embodiment and also makes it possible to apply a reference voltage to the analyte fluid 100 through the transparent reference electrode 400 simply by retaining the analyte fluid 100 on the sensitive membrane 50 without inserting a reference electrode into the analyte fluid 100 after the analyte fluid 100 is retained on the sensitive membrane 50, so that the examination process can be made simple.

Third Embodiment

Figure 5:
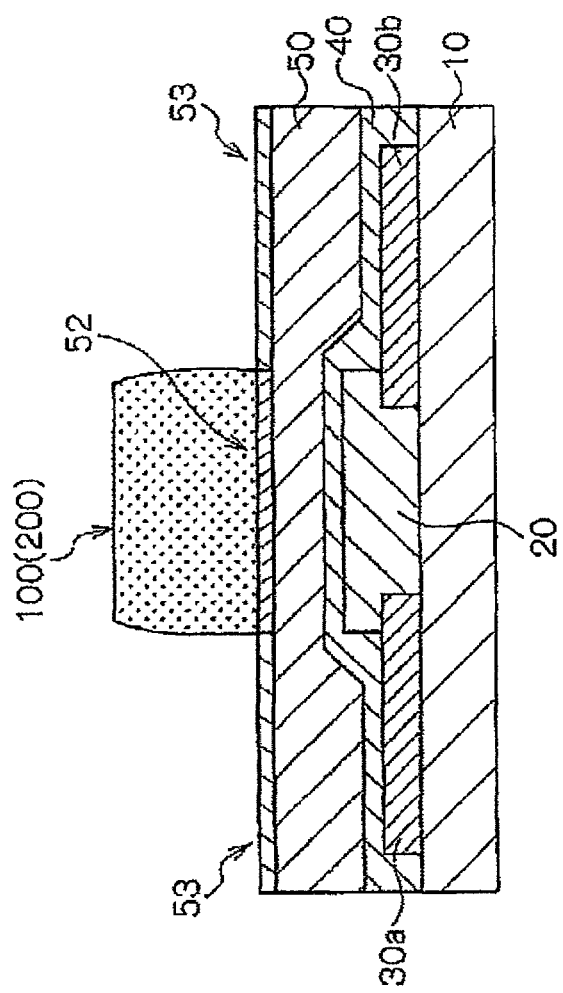
FIG. 5 is a cross-sectional view of an ISFET biosensor according to a third embodiment of the invention.

Next, an ISFET biosensor according to a third embodiment of the invention is described using FIG. 5.

The ISFET biosensor of this embodiment is characterized in that instead of the partition 60 in the first embodiment, the placement region 52 of the sensitive membrane 50 is hydrophilic and a hydrophobic region is provided adjacent to the placement region 52 of the sensitive membrane 50. The other features are the same as the first embodiment. Therefore, the same components are represented by the same reference signs, and the description thereof is omitted.

(Structure of ISFET Biosensor)

First, the structure of the ISFET biosensor of this embodiment is described using FIG. 5. FIG. 5 is a cross-sectional view of the ISFET biosensor of this embodiment.

As shown in FIG. 5, the ISFET biosensor of this embodiment comprises: a substrate 10, a transparent semiconductor film 20 laminated on the substrate 10, source and drain electrodes 30a and 30b formed at both ends of the transparent semiconductor film 20, an insulating film 40 laminated so as to cover the transparent semiconductor film 20 and the source and drain electrodes 30a and 30b, and a sensitive membrane 50 that is laminated on the insulating film 40 and has hydrophobic and hydrophilic regions.

The sensitive membrane 50 has: a placement region (hydrophilic region) 52, which is formed by applying or other methods for providing a material for producing hydrophilicity; and a hydrophobic region 53, which is formed on the sensitive membrane 50 along the periphery of the placement region (hydrophilic region) 52 by applying or other methods for providing a material for producing hydrophilicity so that the analyte fluid 100 can be retained on the placement region (hydrophilic region) 52.

When the sensitive membrane 50 is made of a hydrophilic material, the placement region (hydrophilic region) 52 may be made of the material of the sensitive membrane 50 without using any other material. Alternatively to the above, the placement region (hydrophilic region) 52 may be formed by applying or other methods for providing a hydrophilic material on the surface of the sensitive membrane 50 or by a process including applying a material having low hydrophilicity or hydrophobicity and subjecting it to UV irradiation or other processes.

The hydrophobic region 53 may be formed by applying or other methods for providing a hydrophobic material on the corresponding surface region of the sensitive membrane 50 or by a process including applying a hydrophilic material such as an organic material and subjecting it to a plasma treatment using a tetrafluoromethane gas plasma. In this embodiment, for example, when the sensitive membrane 50 is made of a silicon oxide ($SiO_2$) film having hydrophilicity, the placement region (hydrophilic region) 52 may be made of the silicon oxide film, and the hydrophobic region 53 may be formed by a process including forming an organic material such as a resist at a region corresponding to the hydrophobic region 53 and performing a plasma treatment on the material.

Advantageous Effects

The ISFET biosensor of this embodiment can eliminate the need for the partition 60 and other members for retaining the analyte fluid 100 on the sensitive membrane 50, so that the analyte fluid 100 can be retained on the sensitive membrane 50 without the partition 60 and that the process of manufacturing the biosensor can be simplified.

Modifications

In this embodiment, a reference electrode may be inserted into the analyte fluid 100 as in the first embodiment so that a reference voltage can be applied to the analyte fluid 100, or a reference electrode may be provided adjacent to the sensitive membrane 50 in such a manner as to be insulated from the source and drain electrodes 30a and 30b as in the second embodiment. In such a case, the reference electrode may be formed so as to have hydrophilicity, and a hydrophobic region may also be formed adjacent to the reference electrode. It will be understood that part of the reference electrode may also have hydrophobicity.

Fourth Embodiment

Figure 6:
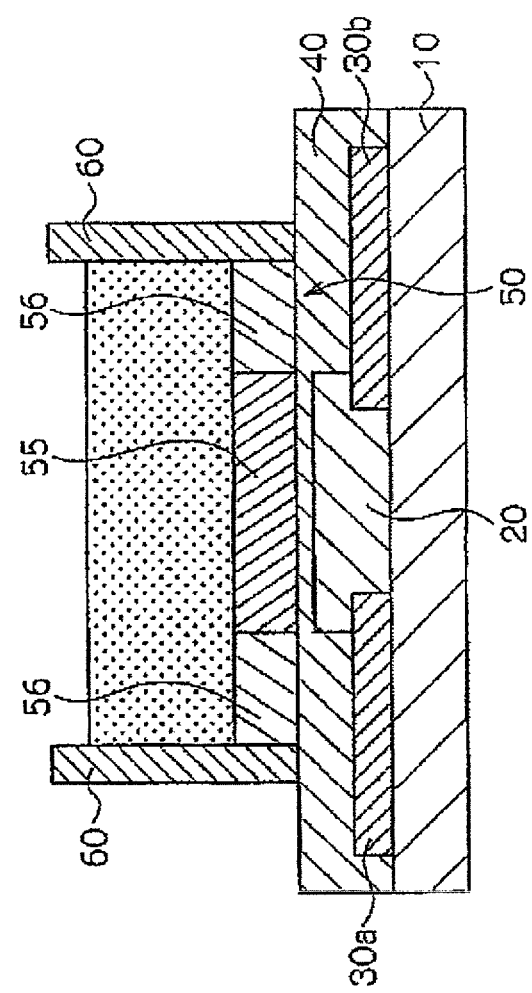
FIG. 6 is a cross-sectional view of an ISFET biosensor according to a fourth embodiment of the invention.

Next, an ISFET biosensor according to a fourth embodiment of the invention is described using FIG. 6.

The ISFET biosensor of this embodiment has the features of the first embodiment and is characterized in that the placement region of the sensitive membrane 50 has cell adhesive properties and that a region adjacent to the placement region of the sensitive membrane 50 has cell adhesion-inhibiting properties. The other features are the same as the first embodiment. Therefore, the same components are represented by the same reference signs, and the description thereof is omitted.

(Structure of ISFET Biosensor)

First, the structure of the ISFET biosensor of this embodiment is described using FIG. 6. FIG. 6 is a cross-sectional view of the ISFET biosensor of this embodiment.

As shown in FIG. 6, the ISFET biosensor of this embodiment comprises: a substrate 10, a transparent semiconductor film 20 laminated on the substrate 10, source and drain electrodes 30a and 30b formed at both ends of the transparent semiconductor film 20, an insulating film 40 laminated so as to cover the transparent semiconductor film 20 and the source and drain electrodes 30a and 30b, a sensitive membrane 50 that is laminated on the insulating film 40 and includes a placement region 55 having cell adhesive properties (hereinafter also referred to as "cell adhesive region") and a region 56 capable of inhibiting cell adhesion (hereinafter also referred to as "cell adhesion-inhibiting region), and a partition 60 for retaining an analyte fluid 100, such as an aqueous solution or liquid culture containing a sample, on the sensitive membrane 50.

The sensitive membrane 50 has: a placement region (cell adhesive region) 55 made of a material with a high strength of adhesion to cells; and a cell adhesion-inhibiting region 56 that is formed along the periphery of the placement region 55 to retain the analyte fluid 100 at the placement region.

The term "cell adhesive properties" means a strength of adhesion to cells, namely a tendency to adhere to cells. The cell adhesive region 55 means a region with good cell adhesive properties, and the cell adhesion-inhibiting region 56 means a region with poor cell adhesive properties. Therefore, when the analyte fluid 100 containing cells is retained on the cell adhesive region 55 and the cell adhesion-inhibiting region 56, which are patterned on the substrate, the cells adhere to the cell adhesive region 55 but do not adhere to the cell adhesion-inhibiting region 56, so that the cells are arranged in a certain pattern on the cell adhesive region 55, namely the placement region.

The cell adhesive properties can also vary depending on the cells to be bound. Therefore, the term "good cell adhesive properties" means that the cell adhesive properties are good for a certain type of cells. Accordingly, two or more cell adhesive regions 55 for two or more types of cells may be laminated on the sensitive membrane 50, and specifically, cell adhesive regions 55 with two or more different levels of cell adhesive properties may be provided.

Specifically, the cell adhesive region 55 may be made of a cell adhesive film, which is produced by a process including: providing a cell adhesion-inhibiting hydrophilic film including an organic compound with a carbon-oxygen bond; and subjecting the film to an oxidation treatment and/or a decomposition treatment to impart cell adhesive properties to the film. The cell adhesive region 55 may be produced by a process including: forming, over the entire surface of the sensitive membrane 50, a cell adhesion-inhibiting hydrophilic film including an organic compound with a carbon-oxygen bond; and then performing an oxidation treatment and/or a decomposition treatment on the region to be adhesive to cells so that the region is modified into the cell adhesive region 55 by imparting cell adhesive properties to the region. The part on which the treatment is not performed corresponds to the cell adhesion-inhibiting region 56.

Alternatively, the cell adhesive region 55 may be made of a hydrophilic film containing a low density of an organic compound with a carbon-oxygen bond. In this case, the cell adhesive region 55 is produced based on the fact that although a hydrophilic film containing a high density of an organic compound with a carbon-oxygen bond has cell adhesion-inhibiting properties, a hydrophilic film containing a low density of such an organic compound has cell adhesive properties. A first region that is more likely to bind to the compound and a second region that is less likely to bind to the compound may be provided on the surface of the sensitive membrane 50, and a film of the compound may be formed on the surface of the sensitive membrane 50, so that the first region turns into the cell adhesion-inhibiting region 56, while the second region turns into the cell adhesive region 55.

On the other hand, the cell adhesion-inhibiting region 56 may be made of a hydrophilic film of an organic compound with a carbon-oxygen bond. This hydrophilic film may be any type of thin film that is produced using a water-soluble or water-swellable organic compound with a carbon-oxygen bond as a main raw material, has cell adhesion-inhibiting properties before being oxidized, and can have cell adhesive properties after being oxidized and/or decomposed. The carbon-oxygen bond refers to any bond formed between carbon and oxygen, which may be not only a single bond but also a double bond. Examples of the carbon-oxygen bond include a C—O bond, a C(=O)—O bond, and a C=O bond.

The main raw material may be a water-soluble polymer, a water-soluble oligomer, a water-soluble organic compound, a surfactant, an amphiphilic agent, or the like. Any of these materials can be physically or chemically crosslinked mutually and can be physically or chemically bonded to the sensitive membrane 50 to form a hydrophilic film. Examples of the water-soluble polymer material include polyalkylene glycol and derivatives thereof, polyacrylic acid and derivatives thereof, polymethacrylic acid and derivatives thereof, polyacrylamide and derivatives thereof, polyvinyl alcohol and derivatives thereof, zwitterionic polymers, and polysaccharides. The molecular shape may be straight-chain, branched, dendrimer, or the like. More specific examples include, but are not limited to, polyethylene glycol, copolymers of polyethylene glycol and polypropylene glycol, such as Pluronic F108™ (manufactured by BASF Corp.) and Pluronic F127™ (manufactured by BASF Corp.), poly (N-isopropylacrylamide), poly(N-vinyl-2-pyrrolidone), poly (2-hydroxyethyl methacrylate), poly (methacryloyloxyethylphosphorylcholine), copolymers of methacryloyloxyethylphosphorylcholine and an acrylic monomer, dextran, and heparin. Examples of the water-soluble oligomer material and water-soluble low-molecular-weight compound include alkylene glycol oligomers and derivatives thereof, acrylic acid oligomers and derivatives thereof, methacrylic acid oligomers and derivatives thereof, acrylamide oligomers and derivatives thereof, saponified vinyl acetate oligomers and derivatives thereof, oligomers of zwitterionic monomers and derivatives thereof, acrylic acid and derivatives thereof, methacrylic acid and derivatives thereof, acrylamide and derivatives thereof, zwitterionic compounds, water-soluble silane coupling agents, and water-soluble thiol compounds. More specific examples include, but are not limited to, ethylene glycol oligomers, (N-isopropylacrylamide) oligomers, methacryloyloxyethylphosphorylcholine oligomers, low-molecularweight dextran, low-molecular-weight heparin, oligo-ethylene glycol thiol, ethylene glycol, diethylene glycol, triethylene glycol, tetraethylene glycol, 2-[methoxy(polyethyleneoxy)-propyl]trimethoxysilane, and triethylene glycol-terminated thiol.

Preferably, the hydrophilic film has high cell-adhesion-inhibiting properties before being treated, and exhibits weak cell adhesive properties after being subjected to an oxidation treatment and/or a decomposition treatment. The average thickness of the hydrophilic film is preferably from 0.8 nm to 500 more preferably from 0.8 nm to 100 µm, even more preferably from 1 nm to 10 and most preferably from 1.5 nm to 1 µm. Preferably, when the average thickness is 0.8 nm or more, the adsorption of proteins or the adhesion of cells is less likely to be affected by the substrate surface region not covered with the hydrophilic thin film. When the average thickness is 500 µl or less, the coating process is relatively easy.

Advantageous Effects

The ISFET biosensor of this embodiment can concentrate the bio-related material 200 on the cell adhesive region 55 and prevent the bio-related material 200 from being deposited on the cell adhesion-inhibiting region 56, so that the effect of the bio-related material 200 present on regions other than the cell adhesive region 55 can be eliminated in the process of detecting the electrical properties and that the electrical properties of the bio-related material 200 adhering to the cell adhesive region 55 can be detected accurately.

Modifications

In this embodiment, a reference electrode may be inserted into the analyte fluid 100 as in the first embodiment so that a reference voltage can be applied to the analyte fluid 100, or a reference electrode may be provided adjacent to the sensitive membrane 50 in such a manner as to be insulated from the source and drain electrodes 30a and 30b as in the second embodiment. In such a case, the cell adhesion-inhibiting region 56 is formed on the reference electrode so that the electrical properties of the bio-related material 200 can be detected accurately.

Fifth Embodiment

Figure 7:
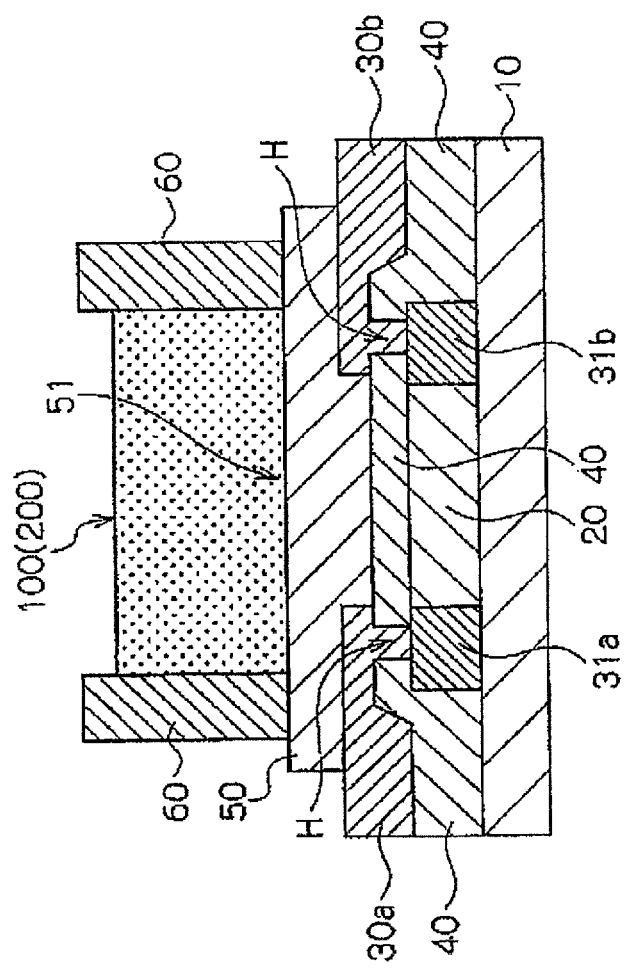
FIG. 7 is a cross-sectional view of an ISFET biosensor according to a fifth embodiment of the invention.

Next, an ISFET biosensor according to a fifth embodiment of the invention is described using FIG. 7.

(Structure of ISFET Biosensor)

First, the structure of the ISFET biosensor of this embodiment is described using FIG. 7. FIG. 7 is a cross-sectional view of the ISFET biosensor of this embodiment.

The ISFET biosensor of this embodiment is characterized in that a coplanar structure is used for the source and drain electrodes 30a and 30b in the first embodiment. The other features are the same as the first embodiment. Therefore, the same components are represented by the same reference signs, and the description thereof is omitted.

As shown in FIG. 7, the ISFET biosensor of this embodiment comprises: a substrate 10, a transparent semiconductor film 20 laminated on the substrate 10, a source-side diffusion region 31a and a drain-side diffusion region 31b which are formed at both ends of the transparent semiconductor film 20, source and drain electrodes 30a and 30b connected to the source-side and drain-side diffusion regions 31a and 31b, respectively, an insulating film 40 laminated so as to cover the transparent semiconductor film 20 and the source-side and drain-side diffusion regions 31a and 31b, a sensitive membrane 50 laminated on the insulating film 40, and a partition 60 that is formed at both ends of the sensitive membrane 50 to retain an analyte fluid 100, such as an aqueous solution or liquid culture containing a sample, on the sensitive membrane 50.

The source-side diffusion region 31a or the drain-side diffusion region 31b is formed by subjecting the transparent semiconductor to a specific treatment with a plasma (e.g., a hydrogen plasma or an argon plasma) for reducing resistance. The source-side diffusion region 31a or the drain-side diffusion region 31b is electrically connected to the source electrode 30a or the drain electrode 30b through a contact hole H formed in the insulating film 40.

Advantageous Effects

Similarly to the first embodiment, when the ISFET biosensor of this embodiment is used, the bio-related material 200 placed on the sensitive membrane 50 can be observed from the substrate 10 side using a microscope or any other optical observation device, while light is applied from above the analyte fluid 100 (from the side opposite to the substrate 10 side), so that the bio-related material 200 can be observed at a high magnification as compared with that achieved when the bio-related material 200 placed on the sensitive membrane 50 is observed from above the analyte fluid 100 and that detection of the electrical properties of the bio-related material 200 and high-magnification observation of the bio-related material 200 can be achieved at the same time.

Modifications

In this embodiment, a reference electrode may be inserted into the analyte fluid 100 as in the first embodiment so that a reference voltage can be applied to the analyte fluid 100, or a reference electrode may be provided adjacent to the sensitive membrane 50 in such a manner as to be insulated from the source and drain electrodes 30a and 30b as in the second embodiment.

The above embodiments are not intended to limit the invention. The above embodiments are described by way of example only, and it will be understood that many variations are possible with substantially the same feature as the technical idea recited in the claims to produce the same effect, and all of such variations are within the scope of the invention.

REFERENCE SIGNS LIST

10: Substrate
20: Semiconductor film
30a: Source electrode
30b: Drain electrode
31a: Source-side diffusion region
31b: Drain-side diffusion region
40: Insulating film
50: Sensitive membrane
51: Placement region
52: Hydrophilic region
53: Hydrophobic region
55: Cell adhesive region
56: Cell adhesion-inhibiting region
60: Partition
100: Analyte fluid
200: Bio-related material
300, 400: Reference electrode

The invention claimed is:

1. A field effect transistor type biosensor, comprising:
   a transparent substrate;
   a transparent semiconductor film laminated on the transparent substrate;
   a source electrode and a drain electrode formed at both ends of the semiconductor film; and
   a sensitive membrane that is laminated on the semiconductor film with an insulating film interposed therebetween and has an upper surface on which a bio-related material contained in an analyte fluid is to be placed,
   wherein the sensitive membrane is an ion sensitive membrane made of at least one material selected from the group consisting of a silicon oxide ($SiO_2$) film, a silicon nitride ($SiN_4$) film, a tantalum oxide ($Ta_2O_5$) film, and an aluminum oxide ($Al_2O_3$) film.

2. The field effect transistor type biosensor according to claim 1, further comprising:
   a first region that has hydrophilicity; and that is formed on the upper surface of the sensitive membrane, on which the bio-related material is to be placed, and on at least above a channel of the semiconductor film; and
   a second region that has hydrophobicity; and that is formed adjacent to the first region and in a horizontal direction perpendicular to a laminating direction of the first region.

3. The field effect transistor type biosensor according to claim 1, further comprising:
   a first region that has cell adhesive properties; and that is formed on the upper surface of the sensitive membrane, on which the bio-related material is to be placed, and on at least above a channel of the semiconductor film; and
   a second region that has cell adhesion-inhibiting properties, comprises a hydrophilic film containing an organic compound with a carbon-oxygen bond, and is formed adjacent to the first region and in a horizontal direction perpendicular to a laminating direction of the first region.

4. The field effect transistor type biosensor according to claim 1, further comprising a reference electrode, wherein the reference electrode is for applying a variable voltage to the analyte fluid and is provided adjacent to the sensitive membrane in such a manner as to be insulated from the source electrode and the drain electrode.

5. The field effect transistor type biosensor according to claim 4, wherein the reference electrode is a transparent electrode.

6. The field effect transistor type biosensor according to claim 1, wherein the transparent semiconductor film comprises a transparent oxide semiconductor.

7. The field effect transistor type biosensor according to claim 1, wherein the source electrode and the drain electrode each comprise a transparent electrode.

8. The field effect transistor type biosensor according to claim 1, wherein the transparent substrate comprises any of glass, PEN, or PET.

9. The field effect transistor type biosensor according to claim 1, wherein the sensitive membrane has a placement region at least on which the bio-related material is to be placed, and which further comprises a partition that is formed around the placement region to retain the analyte fluid on the placement region.

* * * * *